United States Patent [19]
Foltz et al.

[11] Patent Number: 5,401,466
[45] Date of Patent: Mar. 28, 1995

[54] DEVICE FOR THE DIRECT MEASUREMENT OF LOW DENSITY LIPOPROTEIN CHOLESTEROL

[75] Inventors: Mary M. Foltz, Cassopolis, Mich.; Chen-Jung Hsu, Chappaqua, N.Y.; Robert C. Payne, South Bend; James A. Profitt, Goshen, both of Ind.

[73] Assignee: Miles Inc., Elkhart, Ind.

[21] Appl. No.: 69,420

[22] Filed: Jun. 1, 1993

[51] Int. Cl.$^6$ .................... G01N 31/02; G01N 33/92
[52] U.S. Cl. ................................ 422/56; 422/101; 436/71; 436/170; 436/175; 436/177
[58] Field of Search ............ 422/56, 101, 177; 436/71, 86, 175, 169, 170

[56] References Cited

U.S. PATENT DOCUMENTS

| | | | |
|---|---|---|---|
| 4,167,467 | 9/1979 | Golias | 436/71 X |
| 4,185,963 | 1/1980 | Heuck | 436/71 |
| 4,234,317 | 11/1980 | Lucas et al. | 436/71 |
| 4,290,774 | 9/1981 | Girgis et al. | 436/71 X |
| 4,486,531 | 12/1984 | Ziegenhorn et al. | 436/71 X |
| 4,845,198 | 7/1989 | Urdal et al. | 530/387 |
| 4,883,765 | 11/1989 | Tamir et al. | 436/71 |
| 4,923,439 | 5/1990 | Seidel et al. | 436/71 X |
| 4,968,432 | 11/1990 | Antwiler | 436/71 X |
| 5,078,853 | 1/1992 | Manning et al. | 436/71 X |
| 5,118,613 | 6/1992 | McGowan | 436/71 X |
| 5,135,716 | 8/1992 | Thakore | 436/71 X |
| 5,141,872 | 8/1992 | Tanir | 436/71 |
| 5,168,067 | 12/1992 | Miller et al. | 436/71 |
| 5,213,965 | 5/1993 | Jones | 736/71 X |
| 5,215,886 | 6/1993 | Patel et al. | 436/71 X |
| 5,242,833 | 9/1993 | Lawlor et al. | 436/71 |
| 5,286,626 | 2/1994 | Law et al. | 435/285 X |
| 5,290,703 | 3/1994 | Hsu et al. | 436/175 X |

*Primary Examiner*—Jill A. Warden
*Attorney, Agent, or Firm*—Jerome L. Jeffers

[57] ABSTRACT

A dry phase device separates high density lipoprotein (HDL) from a blood (serum or plasma) sample. The device contains a fluid permeable material having dispersed therein finely divided, porous silica or silicate particles as selective absorbant for HDL. By combining the device with a second layer designed to remove very low density lipoproteins/chylomicrons from the blood, and a third layer containing means for quantitative cholesterol detection, there is provided a test device for the direct determination of low density lipoproteins cholesterol.

8 Claims, 1 Drawing Sheet

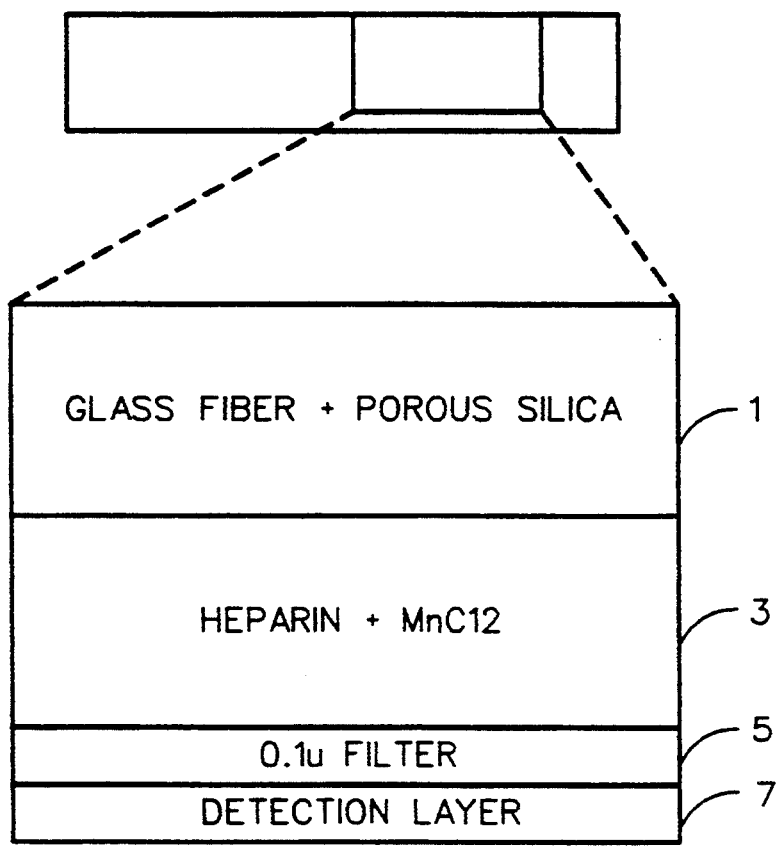

DEVICE FOR THE DIRECT MEASUREMENT OF LOW DENSITY LIPOPROTEIN CHOLESTEROL

BACKGROUND OF THE INVENTION

This invention relates to the field of clinical assay techniques and involves the measurement of low density lipoprotein cholesterol.

Lipoproteins are complex particles comprising proteins and lipids which are found in the circulatory system. One of their functions is to carry water insoluble substances, such as cholesterol and cholesterol esters, for eventual cellular utilization. While all cells require cholesterol for growth, the excess accumulation of cholesterol by cells can lead to certain diseases including atherosclerosis.

There are a variety of classes of lipoproteins in serum which can be classified by their density. These classes include very low density lipoproteins (VLDL), low density lipoproteins (LDL) and high density lipoproteins (HDL). All of these lipoproteins contain varying amounts of cholesterol. A total serum cholesterol determination is a complex sum of the amount that each lipoprotein contributes to the total lipoprotein population of the serum.

While it is known that the amount of total serum cholesterol can be correlated with the incidence of atherosclerosis, evidence from studies of recent years has shown that specific lipoprotein types are more closely associated with the progression of heart disease, including atherosclerosis, than others. More recent studies have implicated LDL as the class of lipoproteins responsible for the accumulation of cholesterol in the cells whereas HDL has been shown to be active in the removal of excess cholesterol from cells. Accordingly, various systems have been proposed for the measurement of cholesterol bearing lipoproteins in general and LDL in particular.

Amorphous silica, i.e. that form of $SiO_2$ which lacks a crystal structure, has been used as an adsorbant since at least as early as World War I when it was considered for use as an absorbant in gas masks. Amorphous silica is broadly divided into three categories: vitreous silica or glass made by fusing quartz; silica M made by irradiating either amorphous or crystalline silica with high speed neutrons and microporous silica. The microparticulate silicas include pyrogenic silicas and silicas precipitated from aqueous solution. Pyrogenic silicas are formed at high temperature by condensation of $SiO_2$ from the vapor phase, or at lower temperature by chemical reaction in the vapor phase followed by condensation.

Silica formed in aqueous solution can occur as sols, gels or particles. A gel has a three-dimensional, continuous structure, whereas a sol is a stable dispersion of fine particles.

Silica gels are classified into three types. Regular density gel is made by gelling in an acid medium, which gives very small particles with high surface area (750–800 $m^2/g$). The average pore diameter is 22–26 Å, and the pore volume is 0.37–0.40 mL/g. Regular density gel contains about 6 wt % water as surface hydroxyl groups, which imparts a high propensity for adsorption of water and other polar molecules. Regular density gel exhibits a high selectivity for polar molecules and possesses a large percentage of small pores. Intermediate density silica has a lower surface area (300–350 $mg^2/g$) but larger pore volume (0.5–1.1 mL/g). The average pore diameter is 120–180 Å in diameter and the particles are larger than those of regular density gel. Because of the large pore size, intermediate density gel has a large capacity for water absorption at high humidities. Low density silica gel has a lower surface area ($<200$ $m^2/g$), larger pore diameter ($>180$ Å) and a larger pore volume ($>1.5$ mL/g) than the other types. It is usually prepared as a very fine powder of extremely low density. When silica is used as an adsorbant, the pore structure determines the gel adsorption capacity. Pores are characterized by specific surface area, specific pore volume (total volume of pores per gram of solid), average pore diameter, pore size distribution and the degree to which entrance to larger pores is restricted by small pores. These parameters are derived from gas or vapor adsorption isotherms, mercury penetration studies, low angle X-ray scattering, electron microscopy, and gas permeability or measurement of the volume of imbibed liquid.

The most common way of preparing silica gel involves acidification of sodium silicate to a pH less than about 10. Silica can be gelled in spherical form by spray-drying, or by spraying droplets onto an immiscible liquid.

Precipitated silica (also called particulate silica) is composed of aggregates of ultimate particles of colloidal size that have not become linked in a massive gel network. Precipitated silicas are either formed from the vapor phase (fumed or pyrogenic silicas) or by precipitation from solution. In the preparation of pyrogenic or fumed silica, sand is vaporized at about 2000° C. On cooling, anhydrous amorphous silica powders form in the presence of a reducing agent such as coke. The amorphous silica sublimes at about 1500° C. to provide Si which is then oxidized to produce particulate $SiO_2$. Pyrogenic or fumed silica is typically used as a thixotropic agent in polyester-glass reinforced plastics; as a reducing and thickening agent in rubber, plastics, silicone and epoxy resins as well as a thickening and gelling agent.

Pure silica is composed of the elements silicon and oxygen. Materials are still referred to as "silicas" after metals, metal oxides or metal salts are added; e.g. flint is a silica with added iron oxide. Glass has a defined composition between $(K,Na)_2O$, $(Ca,Pb)$, $6SiO_2$ and $5(K,Na)_2O$, $7(Ca,Pb)O$ and $36SiO_2$ with a general formula of $(K,Na)O-Si_nO_{2n-1}(CaPb)O-Si_nO_{2n-1}-O(K,Na)$. While all silica based glasses can be called silicas, not all silicas are glass. The HDL adsorbant materials useful in the present invention are porous silica or silicates as these terms are used in their broadest sense.

Microporous silica gels are obtained by heating a hydrated gel at 1000° C. for about 10 hours. Siliceous materials can be made with extremely small pores such as is the case with impervious silica, porous glass and silica used as an adsorbant for certain specific materials. The ability of a material to be adsorbed is determined by the surface composition and pore size of the silica gel. The present invention is concerned with the use of large pore silicas and silicates such as microporous silica, silica gel and controlled pore glass as selective adsorbant materials for HDL from blood serum or plasma.

U.S. Pat. No. 5,141,872 discloses the use of fumed silica for the adsorption of lipoproteins from plasma. The patentees point out that this procedure was known before their invention but claim the improvement of selectively desorbing HDL from the fumed silica by incubating with a detergent containing formulation. Commercially available fumed silicas such as CAB-O-SIL from Cabot Company and Aerosol from Degussa are mentioned as being useful in this procedure.

The diameters of the LDL and VLDL particles are estimated at 220–250 Å and 300–800 Å respectively with chylomicrons being somewhat larger. Since the dimensions of a fumed silica such as Aerosol 380 are less than about 70 Å and the HDL particle is estimated at 100 to 150 Å in diameter, it can be concluded that this binding of lipoproteins as disclosed in U.S. Pat. No. 5,141,872 is based solely on non-specific surface adsorption. Particle size exclusion of the relatively larger lipoprotein particles is not a factor in that method since LDL and VLDL particles are too large to fit in any pores which may exist in the 70 Å particles. This prior art technique achieves its selectivity by desorption in a separate step, whereas the present invention involves the selective adsorption of the smaller HDL particles by the silica gel which, when combined with a mechanism for the separation of VLDL and chylomicrons, provides a fluid sample which can be analyzed for the remaining LDL without further treatment.

SUMMARY OF THE INVENTION

The present invention involves a dry phase device for separating high density lipoprotein from a blood sample. The device comprises a first layer of fluid permeable material having dispersed therein finely divided, porous silica or silicate particles as adsorbant for the HDL. The particles are characterized by having a size of from 1 to 1000$\mu$ in their longest dimension and surface pores of from about 80 Å to 1000 Å in size. The section of silica or silicate containing material can be combined with a second layer of a fluid permeable material bearing reagents for selectively removing very low density lipoproteins and chylomicrons from the blood sample and filtering the complex formed therein through a sub-micron filter to leave low density lipoprotein as the only lipoprotein in the blood sample. When these layers are combined with a third layer comprising a porous matrix containing a reagent system for the quantitative analysis of lipoprotein, there is provided a unitary device for the one step determination of low density lipoprotein.

In an alternative embodiment, the reagents of the first and second layers can be combined into a single layer.

Also included within the scope of the present invention is a method for the one-step determination of low density lipoprotein which involves applying a blood sample to the upper surface of the device described above.

BRIEF DESCRIPTION OF THE FIGURE

The sole FIGURE is an illustration of a dry phase device according to the invention.

DESCRIPTION OF THE INVENTION

The present invention has application in medical diagnostics in situations where it is desirable to remove the HDL component from a mixture of lipoproteins in plasma or serum. Examples of such a technique include using the system as a component of a system where other lipoproteins are also removed to thereby leave only a single lipoprotein which can be directly measured by a cholesterol content assay. Combination of this system with means for removing chylomicrons and very low density lipoprotein (VLDL) results in a direct assay for low density lipoprotein (LDL) which is the lipoprotein of greatest interest.

Alternatively, subtraction of the value for cholesterol in a blood sample, treated as suggested herein, from the value of total cholesterol in the original sample would allow one to deduce the amount of cholesterol carried by HDL in the sample.

In another application, the invention can be used as a means of dispensing lipoprotein interactive reagents in small, precise quantities, particularly where the silica reagent would be used in a subsequent procedure requiring the removal of particular lipoproteins from serum or plasma. For ease of the manufacture of medical diagnostic devices, the lipoprotein interactive reagents could be evenly distributed in a dry sheet. By cutting out a well defined area of the sheet an accurate quantity of the active reagents would be at hand for convenient transfer to the desired container or location.

In its simplest form, the present invention is a layer of fluid permeable material capable of transmitting low- and very low-density lipoproteins but which blocks the transmission of high density lipoprotein in the fluid being tested.

The use of the particulate/porous silica gel immersed in a fluid permeable matrix as disclosed herein is believed to result from a surface interaction with the silica as well as by size exclusion. The HDL component is removable by size exclusion and adsorption, i.e. the HDL is interactive with silica gel having a mean pore diameter greater than the diameter of an HDL particle, and is most useful when the silica pore size is small enough to diminish the interaction of the larger lipoprotein particles such as LDL and VLDL therewith. Silicas of particle size from about 1 to 1000$\mu$ (preferably 3 to 10$\mu$) in their longest dimension and having a range of pore sizes of from 80 Å to 1000 Å (preferably 300 Å to 500 Å) have shown the best selectivity and efficiency for HDL particle removal. A good example of such silica is VYDAC 101 TP from The Separations Group, Hesperia, Calif. Other examples of effective silicas in their order of decreasing effectiveness are as follows:

1) Crosfield Sorbsil C500 40/60;
2) Regis Chemical Co. 023001; 300 Å/3$\mu$ silica
3) E. M. Merck Lichosphere Si 300; 300 Å pore silica
4) E. M. Merck Fractosil 500; 420–490 Å pore silica
5) E. M. Merck Fractosil 200; 200 Å pore silica
6) E. M. Merck Fractosil 1000; 1000 Å pore silica
7) E. M. Merck Lichrosorb Si 100; 100 Å pore silica
8) Whatman Partisil 5; 5$\mu$/66–88 Å pore silica
9) Regis Chemical Co. 024000; 100 Å pore silica In practicing the invention, the silica gel is entrapped in a porous layer by formation of a fibrous network around the particles, as in the case of papers and felts, or by adhesively joining the silica to other fibers or particles which are incorporated easily into the matrix, e.g. by coating a fiber with an adhesive such as cement by running it through a bath of the adhesive followed by contact with the silica particles, curing the cement and washing off loosely bound particles. The fiber strand would then be fragmented for use in a felt or woven into a fabric. Entrapment of the silica gel involving fibers may be assisted by a binder, such as starch or polyvinyl alcohol, to increase the durability of the silica containing layer. Glass is the preferred fiber. Other manmade fibers such as plastics containing hydrophilic groups or natural fibers such as cellulose, wool or silk can be used.

Ideally, the silica containing layer is combined with a separate fluid permeable layer of a matrix having dispersed therein reagents for the selective retention of VLDL and chylomicrons to provide a fluid sample containing only LDL. Suitable agents for this part of the present system include a divalent cation and a polyvalent anion. The divalent cation is typically in the form of $MnCl_2$ or $MgCl_2$, and the polyvalent anion is typically heparin or dextran sulfate. A combination of heparin/$MnCl_2$ is preferred. While the serum or plasma sample being tested may be pretreated to remove VLDL and chylomicrons, a preferred technique involves dispersing the divalent cation/polyvalent anion combination in a porous matrix material such as glass fiber, cellulose or a felt or fabric of natural or man made fibers to provide a dry phase system for the VLDL/chylomicron removal step. The dry matrix material can be readily prepared by dipping the dry matrix substrate in an aqueous solution of the divalent cation/polyvalent anion. It has been discovered that preparation of the matrix base by contacting it with an aqueous system having a polyanion concentration of $\leq$ 0.15 gm/liter of the polyanion and a divalent cation concentration of $\geq$ 350 mM provides the best separation of VLDL and chylomicrons from the blood sample being treated.

This invention is a dry phase assay and can be used to assay for LDL with only small quantities of blood thus allowing the feasibility of a one-drop assay for direct LDL cholesterol measurement. Typically plasma or serum is used although whole blood is suitable when the device is provided with a layer of material capable of filtering erythrocytes. This system provides a complete assay with a single measurement in which the response is derived from an intimate interaction of the analyte of interest.

The method of practicing the present invention is further illustrated by the following examples.

EXAMPLE I

A saturated solution of cornstarch (8.2 mg cornstarch in 2.05 ml water) was prepared by heating to near boiling after which the solution was allowed to cool to room temperature and the insoluble portion was discarded. A 1.12 mL portion of the solution was mixed with 112 mg of long fiber cellulose (Sigma Chemical Co.) and 57 mg of microporous silica (VYDAC 101 TP from The Separations Group). The slurry was cast onto a 1.9 cm diameter suction filter with a nylon mesh mat (CMM 10) in place as a bed for the slurry. When dry, the nylon mat with the fibrous circle was removed from the funnel and the fibrous disk was calendered by overlaying a nylon mesh and applying pressure. The resulting paper like disk was sliced into 0.2×0.2 inch squares and placed over a 0.2×0.2 inch square with openings above and below the stack of layers. Human plasma was applied to the top of the opening and the effluent plasma was collected from the bottom opening by holding a small glass capillary against the membrane. The effluent was analyzed by agarose (Beckman Lipogel) gel electrophoresis (Beckman Paragon system), lipid staining and optical densitometry (Beckman Appraise). Comparison of effluent plasma and the original, untreated plasma showed preferential removal of high density lipoproprotein (HDL) rather than low density lipoprotein (LDL) or very low density lipoprotein (VLDL). These data are set out in Table 1.

TABLE 1

| Lipoprotein | Original | Strip Effluent | Ratio (Effluent/ Original) |
|---|---|---|---|
| HDL | 27.8 | 10.0 | 0.36 |
| VLDL | 6.9 | 7.7 | 1.11 |
| LDL | 33.8 | 34.1 | 1.01 |

EXAMPLE II

A dry reagent strip or well-type device for determining LDL in whole blood samples was fitted with a stack of materials as described below. Referring to the drawing, the stack consists of three layers for LDL selection; a glass felt containing porous silica for filtering red blood cells and capturing HDL (1), a glass fiber layer containing heparin and a manganese salt ($MnCl_2$) (3) and a submicron filter layer (5). Beneath these layers is a cholesterol indicating membrane (7) containing reagents for the breakup of lipoprotein particles, the conversion of cholesterol esters to cholesterol and an ultimate color reaction dependent upon cholesterol concentration. The layers are prepared as follows:

Silica-Glass Felts

In one method, glass wool, 0.33 g, was ground to small fiber segments in 1% aqueous polyvinyl alcohol with a mortar and pestle. The resulting slurry was stirred and poured into a Buchner funnel (sans vacuum) with a tight mesh nylon or commercial glass fiber (Whatman GF/A) layer over the frit and the layer was allowed to settle to a mat. A mixture/slurry of 0.57 g silica (VYDAC 101 TP) (calculated to give 20 mg/$cm^2$ for the final circle area) and 0.33 g glass fiber segments was then poured onto a 20 ml layer of 1% polyvinyl alcohol fluid over the first fiber and allowed to settle. More glass wool, 0.33 g, was ground to small fiber segments in 1% aqueous polyvinyl alcohol with a mortar and pestle. The slurry was stirred and poured onto a 20 ml layer of 1% polyvinyl alcohol fluid over the silica/glass fiber mat and allowed to settle. Vacuum was then applied to draw the fluid and partially dry the mat. The felt mat was then removed along with the support layer and dried in a 50 degree C. forced air oven.

By another method, a slurry of VYDAC silica 101/TP (at 20 mg/$cm^2$ for the final layer), 1% aqueous corn starch and ground Pyrex glass wool (at 35 mg/$cm^2$) was cast onto a pool of 1% aqueous corn starch over commercial glass fiber filter, e.g. Whatman G/F A. The agitated slurry was suctioned down into an even layer and the composite layer was dried in a 50 degree C. air dryer.

The next layer consisted of a glass fiber filter of Whatman PD107 which has been impregnated with heparin and manganese. The impregnation was accomplished by submerging the glass fiber sheet in a solution containing 0.15 mg/ml heparin and 350 mM manganese chloride. The sheet was then wiped free of excess surface clinging solution and dried by heated air. This treated glass fiber material was then layered over a porous filtering layer (0.2 micron pore Loprodyne from Pall Ultrafine Filtration Co.). These layers were then placed on top of a reductive indicator membrane containing reagents for the de-esterification of cholesterol esters and break up of lipoprotein with the ultimate color reaction being derived from cholesterol.

The stack was held firmly in place in a well type device, i.e. a stack of molded plastic parts welded together. This device allows blood to enter at the top of the stack which is positioned over a clear window so that color change can be measured in a small reflectance photometer. This color change is correlated to the lipoprotein remaining in the blood sample when it reaches the detection layer.

EXAMPLE III

Serum was added to a slurry of $MnCl_2$, porcine heparin in the ratio of 2 parts serum to 1 part $MnCl_2$-heparin solution to 111.1 mg silica VYDAC 101TPB4/ml serum. The treated serum sample was mixed by vortexing and allowed to stand at room temperature for approximately 12 minutes before centrifuging at 12,000×g for 3 minutes. The total cholesterol of the infranate was determined on a Roche Cobas Fara Clinical analyzer. The LDL-cholesterol values were obtained by multiplying the infranate total cholesterol by 1.5. Friedewald LDL-cholesterol values were calculated from independent determinations of total cholesterol, HDL-cholesterol and triglycerides according to the formula:

$$LDL\ Chol. = Total\ Chol. - HDL\ Chol. - \frac{Triglycerides}{5}$$

Values obtained using the method of the present invention (direct LDL cholesterol) are compared with those values determined by the Friedewald method. The correlation coefficient between the present method and the Friedewald method was 0.98 as can be determined from Table I.

TABLE I

| Sample Number | Direct LDL Cholesterol (mg/dl) | Friedewald LDL Cholesterol (mg/dL) |
|---|---|---|
| 1 | 177 | 178 |
| 2 | 228 | 232 |
| 3 | 54 | 63 |
| 4 | 92 | 85 |
| 5 | 105 | 121 |
| 6 | 140 | 148 |
| 7 | 145 | 146 |
| 8 | 90 | 115 |
| 9 | 94 | 104 |
| 10 | 101 | 114 |
| 11 | 172 | 182 |
| 12 | 149 | 167 |

To 1.5 mL plastic microcentrifuge vials containing (1) microporous silica [VYDAC 101TP; 270–320 Å, average 300 Å pore size from The Separations Group, Hesperia, Calif.], (2) controlled pore glass [330 Å pore, PG 350-200, Sigma Chemical Co.], (3) controlled pore glass [79 Å pore, PG 75-200] or (4) amorphous fumed silica (non-porous CAB-O-SIL, Grade M5, $2\mu$ aggregates, Cabot Corp.) was added approximately 300 $\mu$L of fresh human serum. A fifth vial containing no silica was used as a control. The contents of the vials are summarized in Table 2.

TABLE 2

|  | Control | Controlled Pore Glass | | Microporous Silica | Fumed Silica | |
|---|---|---|---|---|---|---|
|  |  | PG 75-200 | PG 350-200 | Vydac | Cab-O-Sil | Cab-O-Sil |
| mg/mL | 0 | 111 | 111 | 111 | 11 | 55 |
| mg solid | 0 | 30.5 | 33.6 | 35.1 | 4.4 | 17.0 |
| $\mu$L serum | 300 | 275 | 303 | 316 | 396 | 309 |

Each tube was capped, briefly vortexed, placed in a larger cylindrical tube and simultaneously placed on a rolling hematology mixer (Fisher Scientific) for 15 minutes. The vials were then centrifuged for 8 minutes at 14,000×g. Approximately 225 $\mu$L of clear supernatant fluid was transferred from each vial to a new vial, capped and vortex mixed. The treated samples and the original human serum were analyzed by agarose gel (Beckman Lipogel) electrophoresis (Beckman Paragon System), lipid staining and optical densitometry (Beckman Appraise). Comparison of treated serum results to untreated serum indicated preferential removal of HDL over that of LDL or VLDL by the microporous silicas (VYDAC) and the 330 Å controlled pore glass. There was observed no useful selectivity for HDL by the fumed silica or PG 75-200 controlled pore glass. In this experiment, absorbance units were obtained using the Beckman Appraise Densitometer for each 0.1 mm of the scan of each electrophoresis gel lane. Absorbance at 600 nm was normalized to that of the Hewlett Packard 8452A Spectrophotometer by dividing the raw appraise absorbance data by a factor of 2200. This factor was arrived at by comparison of the response to a blue transparent film standard on each instrument. The absorbance values were converted to % recovery of lipoproteins by the formula 100%×[absorbance ×width (nm) of the experimental lipoprotein band]/[absorbance×width (nm) of the control lipoprotein band]. The results of this experiment, both in terms of absorbance and % recovery of lipoproteins are set out in Tables 3 and 4:

TABLE 3

| | Optical Densitometry of Lipoprotein Bands From Agarose Gel Electrophoresis (Absorbance × mm Units) | | | | | |
|---|---|---|---|---|---|---|
| | | Controlled Pore Glass | | Microporous Silica | Fumed Silica Cab-O-Sil | |
| Lipoprotein | Control | PG 75-200 (79 Å Pores) | PG 350-200 (300 Å Pores) | Vydac | @ 11 mg/mL | 55 mg/mL |
| Chylomicrons | 0.05 | 0.04 | 0.05 | 0.05 | 0.06 | 0.06 |
| HDL | 1.27 | 1.39 | 0.09 | 0.15 | 0.75 | 0.04 |
| VLDL | 0.23 | 0.30 | 0.27 | 0.30 | 0.27 | 0.05 |
| LDL | 1.63 | 1.79 | 1.79 | 1.82 | 1.06 | 0.06 |

TABLE 4

Optical Densitometry of Lipoprotein Bands
From Agarose Gel Electrophoresis
(% Recovery of Lipoproteins)

| Lipoprotein | Controlled Pore Glass | | Microporous Silica Vydac | Fumed Silica Cab-O-Sil | |
|---|---|---|---|---|---|
| | PG 75-200 (79 Å Pores) | PG 350-200 (330 Å Pores) | | @ 11 mg/mL | 55 mg/mL |
| Chylomicrons | —[a] | —[a] | —[a] | —[a] | —[a] |
| HDL | 109 | 7 | 12 | 65 | 4 |
| VLDL | 128 | 114 | 129 | 116 | 21 |
| LDL | 110 | 110 | 112 | 59 | 3 |

[a]Control value too low to give reliable recovery.

For controlled pore glass used at 111 mg/mL, the calculated recovery of HDL and LDL was 109% and 110% respectively for the 80 Å pore material and 7% and 100% respectively for the 300 Å pore material. The microporous silica, VYDAC 101TP, recovered HDL/LDL at 12%/112% when used at 111 mg/mL. Previous experience with fumed silica suggested that lipoprotein removal by 111 mg/mL silica is so complete that no information on selectivity can be gained by electrophoresis of the treated serum. Accordingly, more appropriate amounts of CAB-O-SIL were used. At 55 mg/mL the percent recovery of HDL/LDL was 3%/4% respectively. At a lower level (11 mg CAB-O-SIL/mL serum) the percent recovery HDL/LDL was 59%/65% respectively. Accordingly, it can be seen that while fumed silica removes HDL from serum, it exhibits no useful preference for abstraction of HDL over LDL. The quantity of chylomicron lipoprotein in the original sample was too small to allow a reliable percent recovery number to be calculated.

What is claimed is:

1. A device for separating high density lipoprotein, very low density lipoprotein and chylomicrons from a blood sample containing high density lipoprotein, low density lipoprotein, very low density lipoprotein and chylomicrons which device comprises a layer of fluid permeable material which has dispersed therein finely divided, porous silica gel particles having a particle size of from $1\mu$ to $1000\mu$ in their longest dimension and surface pores of from about 80 Å to 1000 Å in diameter, which silica gel particles demonstrate a selective affinity for high density lipoprotein as compared to low density lipoprotein, very low density lipoprotein and chylomicrons and wherein there is dispersed in the layer of fluid permeable material, or in fluid communication with the layer, a reagent system having affinity for very low density lipoproteins and chylomicrons to form a complex with the very low density lipoproteins and the chylomicrons together with means to separate said complex from the blood sample thereby leaving a blood sample substantially free of all lipoprotein but low density lipoprotein.

2. The device of claim 1 wherein the silica gel particles are from $3\mu$ to $10\mu$ in their longest dimension and the pores have a diameter of from 300 Å to 500 Å.

3. The device of claim 1 wherein the reagent system comprises a polyanion and a divalent cation.

4. The device of claim 3 wherein the reagent system is applied to the fluid permeable material by contacting the fluid permeable material with an aqueous system having dissolved therein a polyanion at a concentration of no greater than 0.15 gm/liter and a polyvalent cation at a concentration equal to or greater than 350 mM.

5. The device of claim 3 wherein the polyanion is heparin and the cation is $Mn^{++}$.

6. The device of claim 3 wherein the polyanion is dextran and the cation is $Mg^{++}$.

7. The device of claim 1 wherein the reagent system is included in a second layer of fluid permeable material located beneath the layer of fluid permeable material having said silica particles dispersed therein and in fluid communication therewith and the means to separate the complex from the blood sample is a submicron filter located beneath said second layer and in fluid communication therewith to filter the very low density lipoprotein-chylomicron/reagent complex to provide a blood sample substantially free of all lipoprotein but low density lipoprotein.

8. The device of claim 7 wherein there is a layer adjacent to and in fluid communication with the submicron filter, which contains a reagent system for the detection of total cholesterol contributed by the low density lipoprotein in the blood sample.

* * * * *